(12) United States Patent
Madsen et al.

(10) Patent No.: US 7,244,756 B2
(45) Date of Patent: Jul. 17, 2007

(54) BENZIMIDAZOL-2-ONE DERIVATIVES AND THEIR USE

(75) Inventors: Lars Siim Madsen, Smørum (DK); Camilla ærteberg Bæk, Allerød (DK); Annette Lauridsen, Søborg (DK); Søren Peter Olesen, Klampenborg (DK)

(73) Assignee: Poseidon Pharmaceuticals A/S, Ballerup (DK)

( * ) Notice: Subject to any disclaimer, the term of this patent is extended or adjusted under 35 U.S.C. 154(b) by 93 days.

(21) Appl. No.: 10/518,554

(22) PCT Filed: Jun. 17, 2003

(86) PCT No.: PCT/DK03/00402

§ 371 (c)(1),
(2), (4) Date: Dec. 22, 2004

(87) PCT Pub. No.: WO2004/002962

PCT Pub. Date: Jan. 8, 2004

(65) Prior Publication Data

US 2005/0250832 A1  Nov. 10, 2005

(30) Foreign Application Priority Data

Jun. 26, 2002 (DK) ............... 2002 00982
Apr. 15, 2003 (DK) ............... 2003 00592

(51) Int. Cl.
*A61K 31/4184* (2006.01)
*C07D 235/26* (2006.01)

(52) U.S. Cl. .................... 514/387; 548/306.4

(58) Field of Classification Search ........... 548/306.4; 514/387
See application file for complete search history.

(56) References Cited

FOREIGN PATENT DOCUMENTS

| EP | 0 477 819 A2 | 4/1992 |
| EP | 0 617 023 A1 | 9/1994 |
| EP | 0 747 354 A1 | 12/1996 |
| WO | WO-01/54771 A2 | 8/2001 |

OTHER PUBLICATIONS

Lawson, Expert Opinion on Investigational Drugs (2000), 9(10), pp. 2269-2280.*
Balinsky, Ph.D., et al., Journal of Pediatric Health Care, (Jan./Feb. 2004), vol. 18, No. 1, pp. 30-34.*
Fox et al., "Activation of Large Conductance Potassium Channels Inhibits the Afferent and Efferent Function of Airway Sensory Nerves in the Guinea Pig", J. Clin. Invest., The American Society for Clinical Investigation, Inc., vol. 99, No. 3, Feb. 1997, 513-519.
Ramnarine et al., "Neuroregulation of Mucus Secretion by Opioid Receptors and KATP and BKCA Channels in Ferret Trachea in vitro", British Journal of Pharmacology (1998) 123, 1631-1638.

* cited by examiner

*Primary Examiner*—Laura L. Stockton
(74) *Attorney, Agent, or Firm*—Birch, Stewart, Kolasch & Birch, LLP

(57) ABSTRACT

Certain 1,5-disubstituted benzimidazol-2-one compounds useful as therapeutic agents. The compounds may be of the Formula I

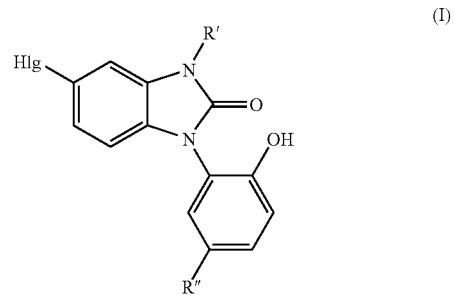

wherein: R' represents hydrogen or alkyl; R" represents halogen or trihalogenmethyl; and Hlg represents halogen; provided, however, that if Hlg is F, then R" is not Cl. Also, use of the 1,5-disubstituted benzimidazol-2-one compounds, or pharmaceutically-acceptable addition salts thereof, in applications that benefit from increasing the blood-brain barrier permeability.

6 Claims, No Drawings

BENZIMIDAZOL-2-ONE DERIVATIVES AND THEIR USE

TECHNICAL FIELD

The present invention provides novel benzimidazol-2-one derivatives useful as therapeutic agents.

BACKGROUND ART

EP 477819 describes benzimidazol derivatives acting on potassium ($BK_{Ca}$) channels, useful for the treatment of e.g. convulsions, asthma, hypertension and ischaemia.

EP 617023 describes benzimidazole derivatives useful as openers of potassium channels, and in particular for the treatment of hypertension, coronary artery spasms, asthma, ischemia, irritable bowl syndrome, spastic bladder, psychosis and convulsions.

EP 747354 describes 3-substituted oxindole derivatives useful as maxi-K ($BK_{Ca}$) channel modulators.

Fox et al. [Fox A J, Barnes P J, Venkatesan P and Belvisi M G: Activation of Large Conductance Potassium Channels Inhibits the Afferent and Efferent Function of Airway Sensory Nerves in the Guinea Pig; *J. Clin. Invest.* 1997 99 (3) 513-519] have shown that NS 1619 (1,3-dihydro-1-[2-hydroxy-5-(trifluoromethyl)phenyl]-5-(trifluoromethyl)-2H-Benzimidazol-2-one), an opener of large conductance calcium-activated potassium ($BK_{Ca}$) channels, inhibits the activity of myelinated and no-myelinated sensory fibers innervating the guinea pig airways via activation of $BK_{Ca}$ channels, and suggest that selective $BK_{Ca}$ channel openers could be of benefit in the treatment of airway disease by reducing both local and central airway reflexes resulting from the excitation and sensitisation of sensory fibers by mediators released during inflammatory conditions. However this reference provides no indication of its usefulness in the treatment of obstructive or inflammatory airway diseases.

Owing to the restrictive transport properties of the brain microvasculature, which forms the blood-brain barrier (BBB) in vivo, transvascular delivery of therapeutic agents to brain tissue represents a particular obstacle, which must be taken into account in the development of therapeutics and routes by which these therapeutics are administered. One way of solving this problem is to apply a combination therapy, in which a vasoactive agent, e.g. the nanopeptide bradykinin or agonists or analogs thereof, is used to increase blood-brain barrier permeability in order to facilitate transport of a co-administered therapeutic agent.

Potassium channels are important regulators of blood vessel tone, and drugs acting on potassium channels have found use as vasoactive agents, which may also be used for facilitating transport of a co-administered therapeutic agent. Thus WO 01/54771 describes the use of potassium channel agonists for delivering a medicament to an abnormal brain region and/or malignant tumour. As only examples of potassium channel activators the compounds NS1619 (1,3-dihydro-1-[2-hydroxy-5-(trifluoromethyl)phenyl]-5-(trifluoromethyl)-2H-benzimidazol-2-one), 1-EBIO (1-ethyl-2-benzimidazolione) and nitric oxide gas are used.

SUMMARY OF THE INVENTION

According to the present invention it has now been found that a certain subgroup of benzimidazol-2-one derivatives, not previously available to the public, happens to be superior in respect of stability, bioavailability, and other properties relevant to drug candidates.

Therefore, in its first aspect the invention provides a benzimidazol-2-one derivative of Formula I

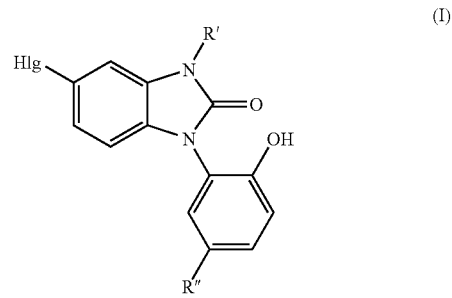

(I)

wherein
R' represents hydrogen or alkyl;
R" represents halogen or trihalogenmethyl; and
Hlg represents halogen;
provided, however, that
if Hlg is F, then R" is not Cl.

In a second aspect the invention provides pharmaceutical compositions comprising a therapeutically effective amount of the 1,5-disubstituted benzimidazol-2-one of the invention, or a pharmaceutically-acceptable addition salt thereof, together with at least one pharmaceutically-acceptable carrier or diluent.

In a third aspect the invention relates to the use of a 1,5-disubstituted benzimidazol-2-one of the invention, or a pharmaceutically-acceptable addition salt thereof, for the manufacture of a medicament for the treatment, prevention or alleviation of a disease or a disorder or a condition of a mammal, including a human, which disease, disorder or condition is responsive to modulation of $BK_{Ca}$ channels.

In a fourth aspect the invention relates to the use of a 1,5-disubstituted benzimidazol-2-one of the invention, or a pharmaceutically-acceptable addition salt thereof, for the manufacture of a medicament useful for increasing the blood-brain barrier permeability.

In a fifth aspect the invention provides a kit-of-parts useful for enhancing the delivery of a medicament to the brain, which kit comprises (i) a benzimidazol-2-one derivative of the invention, and (ii) a therapeutic agent, and (iii) instructions for using the 1,5-disubstituted benzimidazol-2-one derivative for enhancing delivery of the therapeutic agent to the brain.

In a sixth aspect the invention provides methods of treatment, prevention or alleviation of diseases, disorders or conditions of a mammal, including a human, which diseases, disorders or conditions are responsive to modulation of $BK_{Ca}$, channels, and which method comprises the step of administering to such a living animal body in need thereof, a therapeutically effective amount of a benzimidazol-2-one derivative of the invention, or a pharmaceutically-acceptable salt thereof In a seventh aspect the invention provides methods of increasing the blood-brain barrier permeability in a living animal body, including a human, which methods comprise the step of administering to such a living animal body in need thereof, a therapeutically effective amount of a benzimidazol-2-one derivative of the invention, or a pharmaceutically-acceptable salt thereof.

Other objects of the invention will be apparent to the person skilled in the art from the following detailed description and the working examples.

DETAILED DISCLOSURE OF THE INVENTION

Benzimidazol-2-One Derivatives

In its first aspect the invention provides novel benzimidazol-2-one derivative represented by the following Formula I

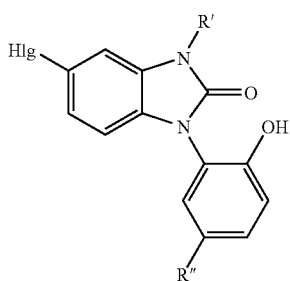

wherein
R' represents hydrogen or alkyl;
R" represents halogen or trihalogenmethyl; and
Hlg represents halogen;
provided, however, that if Hlg is F, then R" is not Cl.

In a preferred embodiment Hlg represents Cl or Br.

In another preferred embodiment R' represents -hydrogen or methyl.

In a further preferred embodiment R" represents halogen or $CF_3$. In a more preferred embodiment R" represents Cl or $CF_3$.

In a most preferred embodiment the benzimidazol-2-one derivative of the invention is.

1-(5-chloro-2-hydroxyphenyl)-5-chloro-1,3-dihydro-2H-benzimidazo-2-one; or 1-(5-trifluoromethyl-2-hydroxyphenyl)-5-chloro-1,3-dihydro-2H-benzimidazo-2-one;

or a pharmaceutically-acceptable salt thereof.

Definition of Substituents

In the context of this invention halogen represents a fluorine, a chlorine, a bromine or an iodine atom. Thus, a trihalogenmethyl group designates e.g. a trifluoromethyl group, a trichloromethyl group or similar trihalogen-substituted methyl groups.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

Pharmaceutically Acceptable Salts

The chemical substance for use according to the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical, compound of the invention and its pharmaceutically acceptable acid addition salt.

Metal salts of a compound for use according to the invention include alkali metal salts such as the sodium salt of a chemical compound of the invention containing a carboxy group.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

The chemical substance for use according to the invention may exist in (+) and (-) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The compound for use according to the invention may also be resolved by the formation of diastereomeric amides by reaction of the chemical compounds of the present invention with an optically active activated carboxylic acid such as that derived from (+) or (-) phenylalanine, (+) or (-) phenylglycine, (+) or (-) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Preparation

The benzimidazol-2-one derivatives of the invention may be prepared by conventional methods for chemical synthesis, e.g. those described in EP 477819, EP 617023 and EP 747354.

Biological Activity

The benzimidazol-2-one derivatives of the invention are potent potassium channel agonists, show an excellent kinetic profile and are chemically stable at physiological relevant conditions. Therefore, in one aspect of the invention the benzimidazol-2-one derivatives may find use as therapeutic agents in the treatment, prevention or alleviation of a disease or a disorder or a condition that is responsive to modulation of $BK_{Ca}$ channels.

In a preferred embodiment the disease, disorder or condition responsive to modulation of $BK_{Ca}$ channels is an obstructive or inflammatory airway disease. In an even more preferred embodiment the obstructive or inflammatory airway disease is an airway hyperreactivity, a pneumoconiosis such as aluminosis, anthracosis, asbestosis, chalicosis, ptilosis, siderosis, silicosis, tabacosis and byssinosis, a chronic obstructive pulmonary disease (COPD), bronchitis, excerbation of airways hyperreactivity or cystic fibrosis, or cough including chronic cough. In a most preferred embodiment the obstructive airway disease is chronic obstructive pulmonary disease (COPD).

In another preferred embodiment the disease, disorder or condition responsive to modulation of $BK_{Ca}$ channels is a cardiovascular disease, in particular atherosclerosis, ischemia/reperfusion, hypertension, restenosis, arterial inflammation, myocardial ischaemia and ischaemic heart disease.

However, the benzimidazol-2-one derivatives of the invention are also found well suited for facilitating the transport of therapeutic substances across the blood-brain barrier, and in particular for facilitating the transvascular delivery of chemotherapeutic agents and viral partides to tumour cells and other abnormal brain tissues.

Therefore, in another aspect, the invention relates to the use of a benzimidazol-2-one derivative of the invention as a facilitating agent, useful for increasing the blood-brain barrier permeability, and thus capable of facilitating transport of a therapeutic substance across the blood-brain barrier, including the blood-tumour barrier found in brain tumours.

In a preferred embodiment of this aspect the benzimidazol-2-one derivative of the invention is used for facilitating agents to an abnormal brain region of brain tissue physiologically affected by injury, trauma, infection, stroke, or ischemia. This abnormal brain region is a region of benign or malignant tumor tissue or other neoplastic diseases or conditions. The malignant tumor may in particular be a glioma, glioblastoma, oligodendroglioma, astrocytoma, ependymoma, primitive neuroectodermal tumor, atypical meningioma, malignant meningioma, neuroblastoma, sarcoma, melanoma, lymphoma, or carcinoma.

When used as a facilitating agent; the benzimidazol-2-one derivative of the invention may be co-administered with the therapeutic agent by any appropriate route, in any convenient way. Preferably, the facilitating agent is administered simultaneously (i.e. contemporaneously or concurrently), or substantially simultaneously (i.e. within about one hour, preferably within 30 minutes, even more preferred within 15 minutes) with the therapeutic agent.

The agents for use according to the invention, i.e. both the facilitating agent and the therapeutic agent, may be administered by any appropriate route, by which the agent is delivered to the blood stream. This is preferably done by intravenous, intramuscular or intra-arterial injection or infusion.

The therapeutic agent for use according to the invention may be any agent or drug. However, preferred therapeutic agents or drugs for use according to the invention are antineoplastic agents, chemotherapeutic agents, cytotoxic agents, DNA expression vectors, proteins, oligonucleotides, nucleotide analogs, antimicrobial agents, interferons, cytokines, cytokine agonists, cytokine antagonists, immunotoxins, immunosuppressants, boron compounds, monoclonal antibodies, adrenergic agents, anticonvulsants, ischemia-protective agents, anti-trauma agents, anticancer chemotherapeutic agents and diagnostic agents.

Preferred chemotherapeutic agents for use according to the invention include:

alkylating agents like the nitrogen mustards (e.g. mechlorethamine, cyclophosphamide, ifosamide, melphalan and chlorambucil), ethylenimines and methylmelamines (e.g. hexamethylmelamine and thiotepa), alkyl sulfonates (e.g. busulfan), nitrosoureas (e.g. carmustine (BCNU), lomustine (CCNU), semustbne (methyl-CCNU) and streptozocin), triazenes (e.g. dacarbazine (DTIC));

antimetabolites like folic acid analogs (e.g. methotrexate), pyrimidine analogs (e.g. fluorouracil, floxuridine and cytarabine), purine analogs and related inhibitors (e.g. mercaptopurine, thioguanine and pentostatin); and natural antimitotic products like vinca alkaloids (e.g. vinblastine and vincristine), epipodophyllotoxins (e.g. etoposide and teniposide), antibiotics (e.g. dactinomycin, daunorubicin, doxorubicin, bleomycin, plicamycin and mitomycin), enzymes (e.g. L-asparaginase), a platinum coordination complex (e.g. cisplatin and carboplatin) and biological response modifiers like the interferons (e.g. interferon-α).

In another preferred embodiment the DNA expression vector is a viral vector, preferably an adenovirus-derived vector or herpes simplex virus-derived vector.

In yet another preferred embodiment the diagnostic agent for use according to the invention may in particular be an imaging or contrast agent, and it may in particular be a radioactively labelled substance, a gallium-labelled substance, or a contrast agent selected from the group consisting of ferrous magnetic, fluorescent, luminescent, and iodinated contrast agents.

When used as a facilitating agent, the benzimidazol-2-one derivative of the invention may preferably, be co-administered with the therapeutic agent for targeting regions of brain tissue physiologically directly affected by a physical or biochemical injury, for example Alzheimer's disease, Parkinson's disease, Parkinsonism, trauma, infection, stroke, brain ischemia, or regions of neoplastic growth within the brain, such as benign or malignant brain tumour tissues.

Pharmaceutical Compositions

In another aspect the invention provides a pharmaceutical composition comprising a therapeutically effective amount of a benzimidazol-2-one derivative of the invention, or a pharmaceutically-acceptable salt thereof, together with at least one pharmaceutically-acceptable carrier, excipient or diluent.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment the invention provides pharmaceutical compositions comprising a chemical substance as described herein, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

In a preferred embodiment the benzimidazol-2-one derivative of the invention find use as therapeutic agents in the treatment, prevention or alleviation of a disease or a disorder or a condition that is responsive to modulation of $BK_{Ca}$ channels.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In a preferred embodiment pharmaceutical composition of the invention is provided in the form of an aerosol formulation in which the active ingredient is provided in a pressurised pack with a suitable propellant.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

In another preferred embodiment the benzimidazol-2-one derivative of the invention may be used as a facilitating agent, and is administered in a way suitable for co-administration with the therapeutic agent.

The facilitating agent of the invention may be co-administered with the therapeutic agent by any appropriate route, in any convenient way. Preferably, the facilitating agent is administered simultaneously (i.e. contemporaneously or concurrently), or substantially simultaneously (i.e. within about one hour, preferably within 30 minutes, even more preferred within 15 minutes) with the therapeutic agent.

The agents for use according to the invention, i.e. both the facilitating agent and the therapeutic agent, may be administered by any appropriate route capable of delivering the agents to the blood stream. This is preferably done by intravenous, intramuscular or intra-arterial injection or infusion.

Pharmaceutical compositions of the invention may in particular be those suitable for parenteral (including cutaneous, subcutaneous, intramuscular, intraperitoneal, intravenous, intraarterial, intracerebral, intraocular injection or infusion) administration.

Preferably the pharmaceutical composition of the invention is a buffer solution acceptable for intravascular infusion into a mammal. Even more preferred a phosphate buffered saline solution.

Further details on techniques for formulation and administration may be found in the latest edition of *Remington's Pharmaceutical Sciences* (Maack Publishing Co., Easton, Pa).

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.01 to about 500 mg of active ingredient per individual dose, preferably of from about 0.1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.01 µg/kg i.v. and 0.1 µg/kg p.o. The upper limit of the dosage range is presently considered to be about 10 mg/kg i.v. and 100 mg/kg p.o. Preferred ranges are from about 0.1 µg/kg to about 10 mg/kg per day i.v., and from about 1 µg/kg to about 100 mg/kg per day p.o.

Kit-of-Parts

In another aspect the invention provides a kit-of-parts, useful for enhancing the delivery of a medicament to the brain.

In a preferred embodiment the kit-of-parts of the invention comprises the benzimidazol-2-one derivative of the invention and a therapeutic agent, together with instructions for using the 1,5-disubstituted benzimidazol-2-one derivative for enhancing delivery of the therapeutic agent to the brain.

Examples of therapeutic agents for use according to the invention are those stated above.

Optionally, the kit also contains other components, such as a particular medicament in any pharmaceutically acceptable formulation, or paraphernalia for injection or infusion, for example syringes, infusion lines, clamps, and/or infusion bags/bottles, which can contain a pharmaceutically acceptable infusible formulation of the potassium channel activator with or without a particular medicament also contained therein.

The materials or components assembled in the kit can be provided to the practitioner stored in any convenient and suitable ways that preserve their operability and utility. For example the components can be in a dissolved, dehydrated, or lyophilized form, and they can be provided at room, refrigerated or frozen temperatures.

Methods of Therapy

In another aspect the invention provides a method for the treatment, prevention or alleviation of a disease or a disorder or a condition of a mammal, including a human, which disease, disorder or condition is responsive to modulation of $BK_{Ca}$ channels, and which method comprises the step of administering to such a living animal body in need thereof, a therapeutically effective amount of a chemical substance as described herein.

In a preferred embodiment the disease, disorder or condition responsive to modulation of $BK_{Ca}$ channels is an obstructive or inflammatory airway disease. In a more preferred embodiment the the obstructive or inflammatory airway disease is an airway hyperreactivity, a pneumoconiosis such as aluminosis, anthracosis, asbestosis, chalicosis, ptilosis, siderosis, silicosis, tabacosis and byssinosis, a chronic obstructive pulmonary disease (COPD), bronchitis, excerbation of airways hyperreactivity or cystic fibrosis.

In its most preferred embodiment the obstructive airway disease is chronic obstructive pulmonary disease (COPD).

In another preferred embodiment the the disease, disorder or condition responsive to modulation of $BK_{Ca}$ channels is a cardiovascular disease. In a more preferred embodiment the cardiovascular disease is atherosclerosis, ischemia/reperfusion, hypertension, restenosis, arterial inflammation myocardial ischaemia or ischaemic heart disease.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which administered, the indication considered, the subject and in particular the body weight of the subject involved, and further the preference and experience of the physician or veterinarian in charge.

In another aspect the invention provides methods of increasing the blood-brain barrier permeability in a living animal body, including a human, which method comprises the step of administering to such a living animal body in need thereof, a therapeutically effective amount of a benzimidazol-2-one derivative of the invention, or a pharmaceutically-acceptable salt thereof.

In a preferred embodiment the method of the invention comprises co-administration of a therapeutic agent. Examples of therapeutic agents for use according to the invention are those stated above.

When used as a facilitating agent, the benzimidazol-2-one derivative of the invention may preferably be co-administered with the therapeutic agent for targeting regions of brain tissue physiologically directly affected by a physical or biochemical injury, for example Alzheimer's disease, Parkinson's disease, Parkinsonism, trauma, infection, stroke, brain ischemia, or regions of neoplastic growth within the brain, such as benign or malignant brain tumour tissues.

EXAMPLES

The invention is further illustrated with reference to the following examples, which are not intended to be in any way limiting to the scope of the invention as claimed.

Example 1

Preparatory Example

N-(3-Chloro-6-methoxy-phenyl)-4-chloro-2-nitroanline (Intermediate compound)

5-chloro-O-anisidine (4.1 g, 26 mmol) in anhydrous N,N-dimethyl formamide (10 ml)-was added sodium hydride (0.9 g 30 mmol) under a nitrogen atmosphere, and the reaction mixture was heat at 45° C. for one hour. Afterwards the mixture was cooled on and ice/water bath. 2,5-Dichloro nitrobenzene (5 g, 26 mmol) was added and the reaction mixture was stirred at 85° C. for 21 hours. The reaction mixture was cooled and poured into water, and the precipitate was isolated by filtration. The precipitate was dissolved in boiling ethyl alcohol (app. 250 ml) and added charcoal. The mixture was filtered, the filtrate was cooled, and the title compound precipitated and isolated by filtration.

4-Chloro-$N^1$-(5-chloro-2-methoxy-phenyl)-benzene-1,2-diamine hydrochloride (Intermediate compound)

N-(3-Chloro-6-methoxy-phenyl)-4-chloro-2-nitroanline (1.9 g, 6.1 mmol) in ethyl alcohol (50 ml) was added Raney nickel, and the reaction mixture was stirred under a nitrogen atmosphere and filtered through cecalite into hydrochloric acid (10 ml of 1 M) in ethyl alcohol. The filtrate was evaporated to dryness and diethyl ether was added. The title compound was isolated by filtration.

5-Chloro-1-(5-chloro-2-methoxy-phenyl)-1,3-dihydro-benzimidazol-2-one (Intermediate compound)

4-Chloro-$N^1$-(5-chloro-2-methoxy-phenyl)-benzene-1,2-diamine hydrochloride (6.3 g, 20 mmol) in tetrahydrofurane (70 ml) was added carbonyldiimidazole (9 g 55 mmol). The reaction mixture was stirred at 60° C. overnight, poured into water (app. 200 ml) and extracted with ethylacetate, and the organic phase was washed with brine and evaporated to an oil. The title compound was crystallized from toluene.

5-Chloro-1-(5-chloro-2-hydroxy-phenyl)-1,3-dihydro-benzimidazole-2-one (Compound 1)

5-Chloro-1-(5-chloro-2-methoxy-phenyl)-1,3-dihydro-benzimidazol-2-one (4 g, 13 mmol) in dichloromethane was cooled to −10° C., and boron tribromide (14.6 ml 1 M solution in dichloromethane 14.6 mmol) was added. The reaction mixture is stirred at room temperature for 6 hours, poured into water (app. 200 ml), and stirred for 15 minutes and filtrated. The title compound was crystallized from toluene/heptane. M.p. 256-257° C.

Example 2

Pharmacokinetic Parameters

In this example the pharmacokinetic parameters of Compound 1 of the invention are compared to those of a close analogue of the prior art, i.e. 1,3-dihydro-1-[2-hydroxy-5-(trifluoromethyl)phenyl]-5-(trifluoromethyl)-2H-Benzimidazol-2-one (i.e. NS1619 described WO 01/54711) herein designated the Reference Compound.

Dosing of Rats

Each compound was dosed to 6 male Wistar rats i.v. and the same for p.o. The rats were sampled as indicated in Table 1, below, but only 3 rats were sampled per time point. The blood samples were centrifuged at 1.300 g at 4° C. for 25 minutes and the resulting plasma samples were stored at <−15° C. pending analysis.

The compounds were dosed as clear solutions in phosphate buffer/Tween 80 (90:10) in a concentration of 3 mg/ml.

TABLE 1

Dosing and sampling of rats

| Compound | Dose p.o. | Dose i.v. | Sampling times p.o. | Sampling times i.v. |
|---|---|---|---|---|
| Ref. Cpd. | 30 mg/kg | 3 mg/kg | 0 min | 0 min |
|  |  |  | 30 min | 10 min |
|  |  |  | 1 h | 30 min |
|  |  |  | 2 h | 1 h |
|  |  |  | 3 h | 2 h |
|  |  |  | 5 h | 4 h |
|  |  |  | 8 h | 7 h |
|  |  |  | 24 h | 24 h |
| Cpd. 1 | 30 mg/kg | 3 mg/kg | 0 min | 0 min |
|  |  |  | 30 min | 10 min |
|  |  |  | 1 h | 30 min |
|  |  |  | 2 h | 1 h |
|  |  |  | 3 h | 2 h |
|  |  |  | 5 h | 5 h |
|  |  |  | 8 h | 7 h |
|  |  |  | 24 h | 24 h |

Sample Preparation

Aliquots of samples, calibrants and QC's (100 µl) were pipetted into 1.5 ml eppendorf tubes. To each tube (except matrix blank) was added 300 µl acetonitrile with internal standards. Matrix blank was added 300 µl acetonitrile without internal standard.

The tubes were shaken on a whirlimixer and then centrifuged for 25 minutes at 16.000 g at 5° C. to precipitate proteins.

An aliquot (200 µl) of the supernatant was transferred to another 1.5 ml eppendorf tube and evaporated to dryness under a gentle stream of nitrogen at 40° C. Then the samples were reconstituted in of mobile phase (initial composition).

Quality Control Samples and Calibration Standards

The results from quality control samples and calibration standards indicated a good quality of data.

TABLE 2

Calibrations and QC's

| Compound | Quality control samples ng/ml, n = 3 | Calibration standards ng/ml, n = 1 | Coefficient of determination | Weighting factor | Comments |
|---|---|---|---|---|---|
| Ref. Cpd. | 2, 80, QCD × 10 (1000), QCD × 100 (10000) | 0.5, 1, 3, 5, 10, 30, 80, 100, 300, 500 (ex.) | 0.9939 | 1/x | All QC's and calibrants except 500 ng/ml were within 15% deviation from nominal concentration |
| Cpd. 1 | $QC_{low}$: 5 ex, $QC_{med}$: 80 ex, QCD × 10 (1000), QCD × 100 (10000) | 0.5, 1, 3, 5, 10, 30, 80, 100 ex, 300, 500, 800, 1000 | 0.9971 | 1/x | $QC_{low}$ and $QC_{med}$ was excluded, but the batch was accepted as 42 samples out of 48 were diluted | ex: Excluded due to deviation >15% to nominal concentration.
QCD: QC diluted

LC-MS/MS Methods

Liquid Chromatography

HPLC column: Waters Xterra MS C8, 2.1×50 mm, 2.5 µm p.s.

Flow: 200 µl/min

Mobile phase A: 5 mM Ammonium acetate pH 6.7 (not pH adjusted).

Mobile phase B: Acetonitrile

Injection volume: 10 µl

Time between injections: 10 min for Ref. Cpd., 11 min for Cpd. 1.

TABLE 3

Elution Gradients

| Gradient of Ref. Cpd. | | Gradient of Cpd. 1 | |
|---|---|---|---|
| 0 min | 20% B | 0 min | 20% B |
| 5 min | 90% B | 1 min | 20% B |
| 6 min | 20% B | 5 min | 90% B |
|  |  | 6 min | 90% B |
|  |  | 7 min | 20% B |

Mass Spectrometry

MS instrument: MicroMass Quattro II

Electrospray: negative ion-mode

Source/desolvation temperature: 110/330° C.

TABLE 4

Multiple Reaction Mode (MRM) Settings

| Compound | Capillary voltage | Cone voltage | Collision energy | Extractor | Transition |
|---|---|---|---|---|---|
| Ref. Cpd. | 2 | 35 | 25 | 1 | 361.0→340.9 |
| Cpd. 1 | 3 | 25 | 21 | 3 | 293.0→249.9 |

Results

Incorporating the data from the rat plasma analyses, the pharmacokinetic parameters were calculated using WinNonLin Professional Edition version 2.0.

TABLE 5

Pharmacokinetic data on Reference Compound and on Compound 1

| Compound | p.o. dose mg/kg | i.v. dose mg/kg | Bio-avail-ability % | $T_{1/2}$ (i.v.) h (time-points) | $T_{1/2}$ (p.o.) h (time-points) | $T_{max}$ h p.o. | $C_{max}$ ng/ml p.o. | $V_d$ L/kg |
|---|---|---|---|---|---|---|---|---|
| Ref. Cpd. | 30 | 3 | 145 | 1.7 h (5 min–5 h) | 2.5 h (3–24 h) | 3 h | 10000 | 1.1 L/kg |
| Cpd. 1 | 30 | 3 | 97 | 0.8 h (5 min–5 h) | 3.2 h (2–24 h) | 0.5 h | 4200 | 1.9 L/kg |

Comments on the Results

As shown in Table 5 above, Compound 1 of the invention shows a faster absorption compared to the reference compound. The $C_{max}$ after p.o. administration is reached after only 30 minutes, compared to 3 hours for that of the reference compound. This means that Compound has a faster onset of action.

The half-life of both compounds after p.o. administration are comparable, although the half-life of Compound 1 seems to be slightly longer.

Example 3

Stability in Solution

In this example the stability of Compound 1 of the invention are compared to those of a close analogue of the prior art, i.e. 1,3-dihydro-1-[2-hydroxy-5-(trifluoromethyl)phenyl]-5-(trifluoromethyl)-2H-Benzimidazol-2-one (i.e. NS1619 described in WO 01/54771) herein designated the Reference Compound.

The stability is determined in neutral ($H_2O$), in basic (0.1M NaOH) and in acidic solution (0.1M HCl).

Experimental Conditions for the Reference Compound Stability in Water 50 ml of water was added to 27 mg of the reference compound. The compound was only partly dissolved. The suspension was stored at 60° C. and after 24 hours 25 ml of methanol was added in order to completely dissolve reference compound. The solution was stored for further 4 hours and then analysed by HPLC (t=28 hours).

Stability in 0.1M HCl 50 ml of 0.1M hydrochloric acid was added to 27 mg of the reference compound. The compound was only partly dissolved. The suspension was stored at 60° C. and after 48 hours 25 ml of methanol was added in order to completely dissolve he reference compound. The solution was stored for further 4. hours and then arialysed by HPLC (t=52 hours).

Stability in 0.1M NaOH 50 ml of 0.1M sodium hydroxide was added to 24 mg of the reference compound. The compound was completely dissolved. The solution was stored at 60° C. and analysed by HPLC after 2 hours (t=2 hours).

Experimental Conditions for Compound 1 Stability in Water 50 ml of water was added to 25 mg of Compound 1. The compound was only partly dissolved. The suspension was stored at 60° C., and after 48 hours, 25 ml of acetonitrile was added in order to completely dissolve Compound 1. The solution was stored for further 24 hours and then analysed by HPLC (t=72 hours).

Stability in 0.1M HCl 50 ml of 0.1M hydrochloric acid was added to 27 mg of Compound 1. The compound was only-partly dissolved. The suspension was stored at 60° C., and after 48 hours, 25 ml of acetonitrile was added in order to completely dissolve Compound 1. The solution was stored for further 24 hours and then analysed by HPLC (t=72 hours).

Stability in 0.1M NaOH 50 ml of 0.1M sodium hydroxide was added to 26 mg of Compound 1. The compound was completely dissolved. The solution was stored at 60° C. and analysed by HPLC after 72 hours (t=72 hours).

The results of the stability determinations are presented in Table 6 below.

TABLE 6

Stability of Compound 1 and Reference Compound Area% (UV 225 nm) of the Test Substance

| | Reference Compound | | Compound 1 | |
|---|---|---|---|---|
| Water, 60° C. | Initial: | 98.4% | Initial: | 99.7% |
| | t = 28 hours: | 96.7% | t = 72 hours: | 99.6% |
| HCl, 60° C. | Initial: | 98.4% | Initial: | 99.7% |
| | t = 52 hours: | 98.4% | t = 72 hours: | 99.6% |
| NaOH, 60° C. | Initial: | 98.4% | Initial: | 99.7% |
| | t = 2 hours: | 0.0% | t = 72 hours: | 99.4% |

The compound of the invention is stable at all conditions.

The reference compound is unstable in neutral to basic solutions. It degrades instantly when dissolved in 0.1 M NaOH, and the compound degraded after 2 hours of storage at 60° C.

The invention claimed is:

1. A 1,5-disubstituted benzimidazol-2-one compound which is
   1-(5-chloro-2-hydroxyphenyl)-5-chloro-1,3-dihydro-2H-benzimidazo-2-one;
   or a pharmaceutically-acceptable salt thereof.

2. A pharmaceutical composition comprising a therapeutically effective amount of the 1,5-disubstituted benzimidazol-2-one compound of claim 1, or a pharmaceutically-acceptable addition salt thereof, together with at least one pharmaceutically-acceptable carrier or diluent.

3. The pharmaceutical composition of claim 2, which composition also comprises a chemotherapeutic agent.

4. A method of increasing the blood-brain barrier permeability a mammal, including a human, which method comprises the step of administering to such a living animal body in need thereof, a therapeutically effective amount of a 1,5-disubstituted benzimidazol-2-one compound of claim 1, or a pharmaceutically-acceptable salt thereof.

5. The method according to claim 4, which method comprises co-administration of a chemotherapeutic agent.

6. A kit-of-parts useful for enhancing the delivery of a medicament to the brain, which kit comprises:

the 1,5-disubstituted benzimidazol-2-one compound of claim 1;

a chemotherapeutic agent; and instructions for using the 1,5-disubstituted benzimidazol-2-one compound for enhancing delivery of the chemotherapeutic agent to the brain.

* * * * *